United States Patent
Berthon-Jones

(10) Patent No.: US 10,046,127 B2
(45) Date of Patent: *Aug. 14, 2018

(54) PRESSURE SUPPORT VENTILATION OF PATIENTS

(75) Inventor: Michael Berthon-Jones, Leonay (AU)

(73) Assignee: RedMed Limited (AU)

(*) Notice: Subject to any disclaimer, the term of this patent is extended or adjusted under 35 U.S.C. 154(b) by 815 days.

This patent is subject to a terminal disclaimer.

(21) Appl. No.: 13/540,169

(22) Filed: Jul. 2, 2012

(65) Prior Publication Data

US 2013/0104898 A1  May 2, 2013

Related U.S. Application Data

(63) Continuation of application No. 12/355,890, filed on Jan. 19, 2009, now Pat. No. 8,225,789, which is a
(Continued)

(51) Int. Cl.
*A61M 16/00* (2006.01)
*A61M 16/06* (2006.01)

(52) U.S. Cl.
CPC .... *A61M 16/0057* (2013.01); *A61M 16/0069* (2014.02); *A61M 16/024* (2017.08);
(Continued)

(58) Field of Classification Search
CPC .......... A61M 16/00; A61M 2016/0036; A61M 2230/00; A61M 2230/202
See application file for complete search history.

(56) References Cited

U.S. PATENT DOCUMENTS 636,983 A    11/1899   Hanson
4,619,269 A  10/1986   Cutler et al.
(Continued)

FOREIGN PATENT DOCUMENTS

EP    0753320 A1    1/1997
EP    0901798 A1    3/1999
(Continued)

OTHER PUBLICATIONS

EP Application No. 02750638.5 Office Action, European Patent Office, dated Nov. 4, 2010.
(Continued)

*Primary Examiner* — LaToya M Louis
(74) *Attorney, Agent, or Firm* — Lerner, David, Littenberg, Krumholz & Mentlik, LLP

(57) ABSTRACT

A methodology and apparatus for determining ventilator settings including an end expiratory pressure setting, pressure swing, resistive unloading and target ventilation for delivering ventilatory support based upon generalized patient ventilation characteristics and/or disease classifications. An apparatus may be programmed with the instructions to accomplish the methodology interactively by prompting the user/physician during setup and calculating settings based upon measurements or input responses. Pre-assigned values associated with ventilation characteristics or disease classifications may be combined with a base pressure value or measured values to provide patient customized settings or adjustments to determine pressure levels for the delivery of ventilatory support.

28 Claims, 7 Drawing Sheets

Related U.S. Application Data continuation of application No. 10/311,920, filed as application No. PCT/AU02/00961 on Jul. 18, 2002, now Pat. No. 7,520,279.

(60) Provisional application No. 60/306,972, filed on Jul. 19, 2001.

(52) U.S. Cl.
CPC ..... *A61M 16/06* (2013.01); *A61M 2016/0021* (2013.01); *A61M 2016/0036* (2013.01); *A61M 2230/202* (2013.01)

(56) References Cited

U.S. PATENT DOCUMENTS

| | | | |
|---|---|---|---|
| 5,107,830 A | 4/1992 | Younes | |
| 5,199,424 A | 4/1993 | Sullivan et al. | |
| 5,320,093 A | 6/1994 | Raemer | |
| 5,522,382 A | 6/1996 | Sullivan et al. | |
| 5,682,877 A | 11/1997 | Mondry | |
| 5,738,090 A | 4/1998 | Lachmann et al. | |
| 5,752,509 A | 5/1998 | Lachmann et al. | |
| 5,794,615 A | 8/1998 | Estes | |
| 5,800,361 A | 9/1998 | Rayburn | |
| 5,803,066 A | 9/1998 | Rapoport et al. | |
| 6,071,237 A | 6/2000 | Weil et al. | |
| 6,148,814 A | 11/2000 | Clemmer et al. | |
| 6,257,234 B1 | 7/2001 | Sun | |
| 6,273,088 B1 | 8/2001 | Hillsman | |
| 6,578,575 B1 * | 6/2003 | Jonson | 128/204.21 |
| 6,644,312 B2 | 11/2003 | Berthon-Jones et al. | |
| 6,694,977 B1 * | 2/2004 | Federowicz et al. | 128/204.18 |
| 6,845,773 B2 | 1/2005 | Berthon-Jones et al. | |
| 6,920,875 B1 * | 7/2005 | Hill | A61M 16/00 128/204.18 |
| 6,962,155 B1 * | 11/2005 | Sinderby | A61M 16/0051 128/204.18 |
| 7,089,937 B2 | 8/2006 | Berthon-Jones et al. | |
| 2001/0029339 A1 | 10/2001 | Orr et al. | |
| 2006/0237015 A1 | 10/2006 | Berthon-Jones et al. | |

FOREIGN PATENT DOCUMENTS

| | | |
|---|---|---|
| EP | 1132106 A2 | 9/2001 |
| JP | 09-024099 A | 1/1997 |
| JP | 11-114066 A | 4/1999 |
| WO | 92/04865 A1 | 4/1992 |
| WO | 97/28838 A1 | 8/1997 |
| WO | 98/12965 A1 | 4/1998 |
| WO | 99/45452 A2 | 9/1999 |
| WO | WO 9951292 A1 * | 10/1999 |

OTHER PUBLICATIONS

Martin J. Tobin, Ed, "Principles and Practice of Mechanical Ventilation", 993-995 (1994).

* cited by examiner

VENTILATOR

PRESSURE SUPPORT VENTILATION OF PATIENTS

CROSS-REFERENCE TO RELATED APPLICATIONS

The present application is a continuation of U.S. patent application Ser. No. 12/355,890, filed on Jan. 19, 2009, which is a continuation of U.S. patent application Ser. No. 10/311,920, filed on Dec. 18, 2002, which application is a national phase entry under 35 U.S.C. § 371 of International Application No. PCT/AU02/00961 filed Jul. 18, 2002, which claims priority from U.S. Provisional Application No. 60/306,972, filed Jul. 19, 2001, all of which are hereby incorporated herein by reference.

FIELD OF THE INVENTION

This invention relates to methods and devices for providing ventilatory assistance to a patient. More specifically, the invention involves an improved method and device for adjusting the device settings to provide ventilation to satisfy a patient's respiratory needs.

BACKGROUND OF THE INVENTION

In untreated patients with lung, chest wall, or control abnormalities, blood gases typically deteriorate somewhat in NREM sleep, and then deteriorate much further in REM sleep. This deterioration is likely due to multiple causes, including:
1. Increased upper airway resistance due to pharyngeal collapse.
2. Loss of cough and sigh, leading to sputum retention and atelectasis.
3. Postural effects on V/Q.
4. Reduced tonic or chemoreflex drive to the diaphragm, particularly in REM.
5. Reduced tonic or chemoreflex drive to intercostals, abdominal expiratory muscles, and other accessory muscles.
6. Possible REM-specific changes in pulmonary blood flow distribution.

Pharyngeal collapse is most profound in REM sleep. There is evidence that the reduction in ventilation in NREM sleep is entirely due to pharyngeal collapse, and not to a reduction in chemoreflex drive to the diaphragm. Increased pharyngeal resistance is treated with CPAP, or more generally with positive pressure sufficient to splint the airway at zero flow, plus additional inspiratory pressure sufficient to compensate for resistive and Bernoulli pressure drop.

Reducing the work of breathing and resting the respiratory muscles by providing ventilatory support, particularly if delivered during sleep, can have a number of direct and indirect potential benefits. These benefits include:
Prevention of muscle fatigue with inefficient contraction.
Reduced oxygen cost of breathing.
Reduction of dyspnea.
Improved sleep, with fewer respiratory arousals.
Improved sleep should in turn reduce metabolic rate, $CO_2$ production and oxygen consumption, directly and indirectly by reduced rolling around, fidgeting, etc., leading to either better blood gases or reduced need for ventilatory support. It is also worthwhile in its own right because of improved quality of life.

However, there are some untoward effects of ventilatory support on the patient as follows:
 1. Barotrauma
 For ventilators delivering less than 35 $cmH_2O$ peak pressure, barotrauma is largely confined to patients with adult respiratory distress syndrome (due to high shear stresses) and to patients with a history of pneumothorax or emphysematous bullae.
 2. Reduced Cardiac Output
 Even in normal subjects, 10 $cmH_2O$ nasal CPAP can produce a 10% reduction in cardiac output, and high levels of positive pressure, particularly in patients who are fluid depleted, can produce a profound reduction in cardiac output. Conversely, in patients with cardiac failure and fluid overload (pulmonary capillary wedge pressure in excess of 15 $cmH_2O$), nasal CPAP actually increases cardiac output, probably by reducing transmural pressure.
 3. Mouth Leak
 Mouth leak is present to some extent in most patients being treated with ventilatory support. A mouth leak of 0.4 L/sec causes severe sleep disruption, loss of ventilatory support, loss of supplemental oxygen, and loss of end expiratory splinting pressure. Such a leak is present in perhaps 50% of subjects. Mouth leak also causes increased nasal resistance. This is a reflex response to drying and cooling of the nasal mucosa by a unidirectional flow of air in the nose and out the mouth.
 A chin strap is only very partially effective in controlling mouth leak. Heated humidification can partially treat the, drying of the nasal mucosa but not the other aspects of the problem. Where tolerated, a full face mask is the preferred treatment.
 4. Glonic Closure
 Rodenstein and colleagues have shown that over ventilation leads to a progressively tight closure of the vocal cords, both awake and asleep, and that this fact must be taken into account when providing noninvasive ventilation.
 The details are not well understood; it is not known whether the glottic closure is purely passive or involves active adduction, whether it is abolished by anaesthesia, whether it is present in REM, whether it is due to airway or arterial hypocapnia, or whether it is produced by sleepstate specific changes in set-point. Unlike passive pharyngeal collapse, it is not known whether vocal cord closure responds to CPAP, but if it is an active closure it would be expected to be extremely refractory to CPAP.
 5. Increased Deadspace
 Positive pressure will alter the distribution of pulmonary blood flow, tending to reduce blood flow to poorly ventilated units (beneficial reduction in physiological shunt) and also to well-ventilated units (pathological increase in deadspace). In patients in whom there is much blood flow to poorly perfused lung units, for example patients with obesity hypoventilation syndrome, this reduction in physiological shunt but increase in deadspace can be of net benefit, whereas in patients with much ventilation to poorly perfused regions, such as "pink puffers", the net effect can be detrimental.
 6. Discomfort
 A goal of a ventilator is to relieve dyspnea. However, it can cause considerable discomfort, by various mechanisms:
 Distension of upper airway structures.
 Swallowing of air (particularly once pressures exceed 20 $cmH_2O$).
 Mask discomfort.
 Leak, particularly mouth leak.
 Patient-machine asynchrony.

We might expect that as the degree of support is increased from zero towards that which will perform 100% of eupneic respiratory work, the sense of dyspnea due to having to do an abnormally high amount of respiratory work, and the sense of distress due to excess chemoreflex stimulation should both decrease towards zero. However, discomfort from all the causes bullated above will increase. There is no literature on the rate of trade-off between the two sources of distress, but it is apparent that the patient should feel most comfortable at a degree of support which is less than 100% support. Very preliminary unpublished work by the current author, in which normal subjects breathe through a high external resistance (8 cmH$_2$O/L/sec) with 200 ml added deadspace, and are then treated with bilevel support, the patient feels most comfortable at about 50% support. The optimum point may of course be quite different in a patient with actual lung or chest wall disease, or with forms of support other than bilevel.

7. Patient-Machine Asynchrony

Patient-machine asynchrony can be due to a number of factors, including:

Leaks.

Long respiratory time constant (e.g. in patients with severe chronic airflow limitation ("CAL")).

Intrinsic PEEP.

Leaks, and particularly variable leaks, cause asynchrony because the airflow measured by the device does not equal the patient respiratory airflow. With a device of the invention, leaks start to become a problem at about 0.2 L/sec, and are a severe problem by 0.4 L/sec. At 0.6 L/sec, the device will probably not really be benefiting the patient. Keeping the leak much below 0.2 L/sec is technically very demanding and not generally practicable. Therefore, while one wants to keep the leak as low as possible with reasonable investment of effort, 0.2 L/sec is a reasonable balance between effort and results.

Patient-machine asynchrony is particularly a problem in patients with long respiratory time constants being treated with high degrees of support. This is because even true respiratory airflow no longer equals patient effort. For example, at the end of the patient's inspiratory effort, the lungs have not yet equilibrated to the high inspiratory pressure and continue to fill. This prevents correct triggering into expiration. The patient must actively expire in order to terminate the inspiration. The higher the degree of support results in greater difficulty with the phenomenon. Therefore, one wants to avoid excessive support.

Intrinsic PEEP causes a kind of asynchrony because the patient must generate a considerable inspiratory effort before any flow is generated. Intrinsic PEEP due to dynamic airway compression may be evident from an expiratory flow-time curve, in which there is a brief period of very high expiratory flow, followed by a very prolonged expiratory flow plateau at a much lower flow. Treatment is to increase expiratory pressure (particularly late expiratory pressure) until the curve shape normalizes.

Thus, with these seven effects in mind, the goals of automatic ventilatory positive airway pressure may generally be summarized to include the following:

1. To guarantee an adequate alveolar ventilation during sleep.
2. To maximize wake comfort.
3. To maximize depth of sleep.
4. To minimize cost of initiation of therapy.

Directed towards the above goals, a ventilator device in accordance with the invention may provide:

1. Servo-control of minute ventilation to equal or exceed a chosen target.
2. Unloading of much of the spontaneous resistive work if the subject exceeds the chosen target.
3. A smooth and physiological pressure waveform whose minimum amplitude will unload much but not all of spontaneous elastic work if the subject just exceeds the chosen target.
4. A mechanism for automatically establishing the target during an awake learning session in subjects who have adequate PCO$_2$ in the daytime and who deteriorate only during sleep.

However, even sophisticated ventilatory devices with a high degree of automatic processing developed to meet one or more of these goals such as the devices disclosed in International Publication No. WO 98/12965 and International Publication No. WO 99/61088 still often require the setting of controls to accommodate a particular patient's needs before beginning use. Absent a uniform methodology for adjusting the settings of such a device, the delivery of the appropriate degree of pressure support to the patient may not be optimal.

BRIEF SUMMARY OF THE INVENTION

Accordingly, keeping with the above goals and/or other goals that will be apparent to those skilled in the art, the invention is a novel methodology for adjusting the settings of a ventilator. In one form of the invention, a pressure setting to maintain a positive end expiratory pressure is determined using assigned adjustment pressure values representing generalized patient ventilation characteristics such as obesity, sleepiness, chronic airflow limitation, etc. As a result of responses to inquiries, the assigned adjustment pressures are added to a starting or default pressure setting. The starting pressure setting is preferably about 4 cmH$_2$O and the adjustment pressures preferably range from about 1-2 cmH$_2$O. The resulting range is about 4-10 cmH$_2$O. Support pressure may then preferably be delivered in accordance with a pressure formula that accounts for resistive unloading and a determined respiratory phase as a continuous phase variable. The methodology may be implemented by an apparatus programmed to execute the methodology interactively by prompting a user/physician to respond to the predetermined inquiries and then calculate the adjustment based upon the input responses.

Therefore, the invention includes a method or apparatus for determining a setting for a ventilator to deliver support to a patient to maintain a positive end expiratory pressure comprising the steps of selecting an initial pressure value; prompting for responses to queries about a patient concerning generalized ventilation characteristics; and calculating a positive end expiratory pressure from said initial pressure value and a set of adjustment pressure values based upon said responses to said queries, said adjustment pressure values representing general ventilation characteristics.

A further embodiment of the invention involves determining a setting for a ventilator to deliver support to maintain a pressure swing in a specified range. The swing is preferably chosen to do about 50% of a patient's elastic work. In the method an initial pressure value is selected and based upon responses prompted to determine degrees of severity, for example, mild, moderate and severe, of restrictive mechanical abnormality of the lung or chest wall of a patient, a pressure swing setting is calculated with the initial pressure and pressure values assigned to the different degrees of severity. The preferred assigned values in a range of about 2-6 cmH$_2$O lead to a swing of about 5-9 cmH$_2$O. As with the other embodiments of the invention, the methodology may be manual or implemented via interactive responses to prompts issued from an automated apparatus.

Therefore, the invention includes a method or apparatus for determining a setting for a ventilator to deliver support to maintain a pressure swing in a specified range chosen to do about half of a patient's elastic work comprising the steps of selecting an initial pressure value; prompting for a response to a query about a patient concerning degrees of severity of a restrictive mechanical abnormality of lung or chest wall; and calculating a pressure swing from said initial pressure value and a set of adjustment pressure values based upon said response to said query, wherein said set of adjustment pressure values represent degrees of severity of a restrictive mechanical abnormality of lung or chest wall.

Another embodiment of the invention involves a methodology for determining resistive unloading for a ventilator setting to deliver support. The setting is preferably chosen to unload about 50% to 80% of a subject's resistive work. The method involves the use of assigned resistive unloading pressure values representing degrees of severity of one or more diseases, for example, restrictive disease and/or obstructive disease. By prompting for a response to determine whether the patient suffers from a particular degree of severity, for example, mild, moderate or severe, the setting can be determined from the response by using the assigned pressure value. In the preferred embodiment, the pressure values for mild, moderate and severe obstructive disease are in a range of about 4-8 cm H$_2$O/L/sec. and preferably 4, 6 or 8 cmH$_2$O respectively. The pressure values for mild, moderate and severe restrictive disease are in a range of about 3-8 cm H$_2$O/L/sec. and preferably 3, 6 or 8 cmH$_2$O respectively. The method may be performed manually. Alternatively, a ventilator device is programmed with the instructions to accomplish the method interactively.

Therefore, the invention includes a method or apparatus for determining a resistive unloading setting for a ventilator to deliver support to unload about 50% to 80% of a subject's resistive work comprising the steps of prompting for a response to at least one query to determine the subject's degree of severity of restrictive disease and obstructive disease; and setting a resistive unloading value to one of a set of assigned pressure values based upon said response to said at least one query, wherein said set of assigned pressure values represents degrees of severity of restrictive disease and obstructive disease.

In one form of the invention, a target ventilation setting is determined as a function of measured PCO$_2$. In the invention, a patient's ventilation is measured over time during a learning period in which ventilatory support is provided and a target ventilation is derived as a function of the measured ventilation. The patient's arterial partial pressure of CO2 is also measured. The target ventilation is then adjusted as a result of the measured arterial partial pressure. Preferably, the measure is compared to a threshold PCO$_2$ and the target ventilation may be increased or decreased based upon the comparison. The target ventilation may then be increased or decreased based upon a fixed percentage of the absolute value of the difference between the measured PCO$_2$ and the threshold PCO$_2$. In the preferred calculation, the threshold is about 50 mmHg.

Therefore, the invention includes a method or apparatus for determining a target ventilation setting of a ventilator comprising the steps of delivering ventilatory support during an awake learning period to a patient; measuring the patient's ventilation over time during a learning period; measuring the patient's partial pressure of CO$_2$; calculating a target ventilation as a function of a measure of ventilation; and adjusting said target ventilation as a function of a measure of partial pressure.

DETAILED DESCRIPTION

Figure 1:
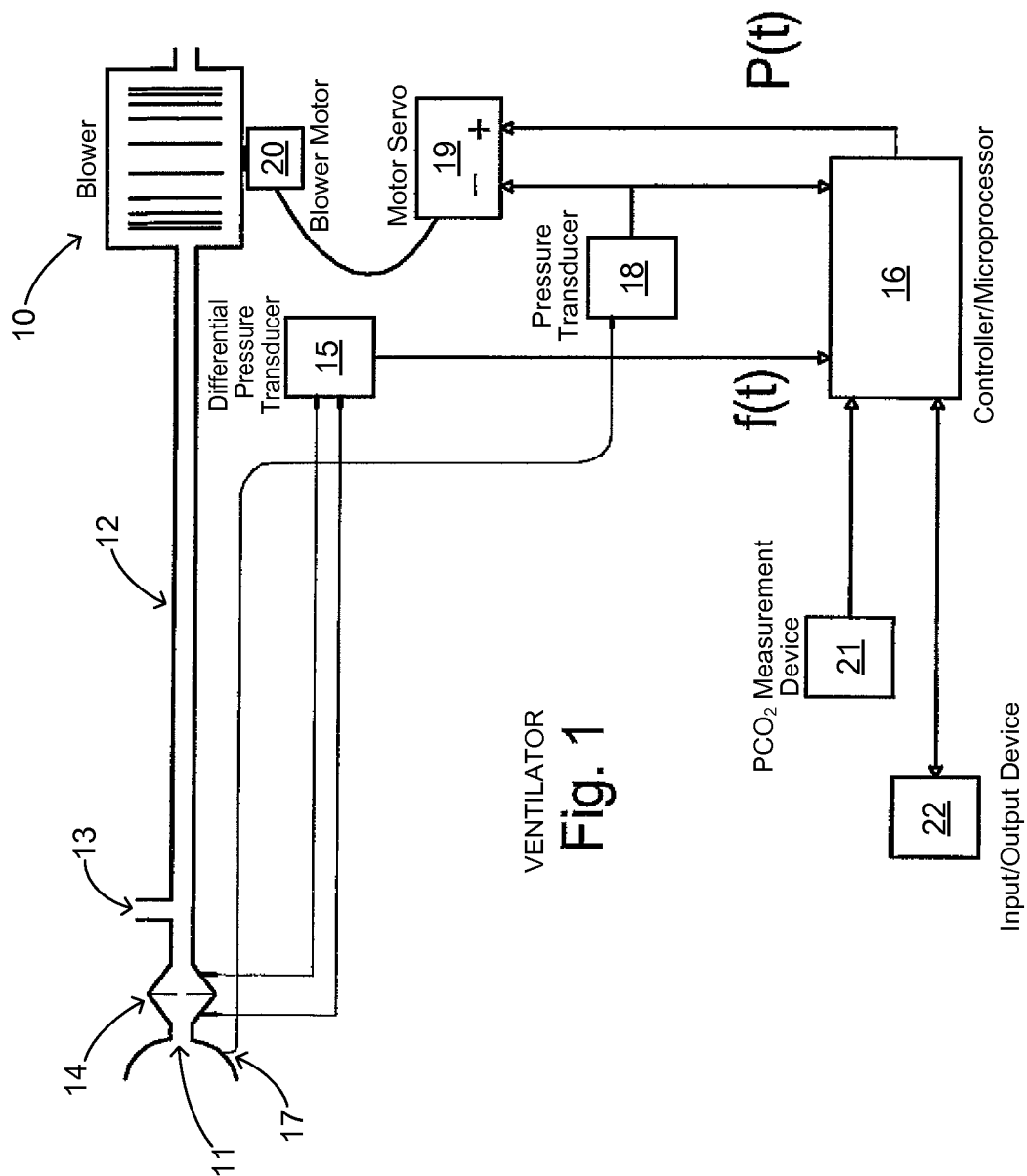
FIG. 1 depicts a ventilator apparatus operable for performing the methodology of the invention.

A servo-controlled ventilator useful for accomplishing the invention is shown in FIG. 1. A blower 10 supplies air under pressure via delivery tube 12 to a mask 11 or via another such device for providing flow to a patient's respiratory system. Exhaust gas is vented via exhaust 13. Mask flow is preferably measured using pneumotachograph 14 and differential pressure transducer 15 to derive flow signal f(t). Mask pressure is measured at pressure tap 17 using pressure transducer 18. Flow and pressure signals are sent to a controller or microprocessor 16 including a memory which implements the processing described herein to derive a pressure request signal P(t). Programmed instructions accessible to the microprocessor are coded on integrated chips in the memory of the device or may be loaded as software and stored by some other data storage medium of conventional design (not shown). The actual measured pressure and pressure request signal P(t) are fed to motor servo 19 which controls blower motor 20 to produce the desired instantaneous mask pressure. Optionally, an automated PCO$_2$ measurement device 21 or other non-invasive blood gas monitor/device for measuring PCO$_2$ may be linked to provide an input data signal to the microprocessor 16, for example, a device as taught in U.S. Pat. No. 5,630,413, the disclosure of which is incorporated by reference. Optional input and/or output devices 22 may be included to display output signals and enter input signals for the microprocessor 16. Various appropriate input and output devices such as keypads and display screens and other alternatives are known in the art.

An example of this type of servo-controlled ventilator is the subject of International Publication No. WO 98/12965, which is also disclosed in related U.S. application Ser. No. 08/935,785. An additional example is disclosed in International Publication No. WO 99/61088, which is also contained in related U.S. application Ser. No. 09/316,432. The foregoing U.S. applications are hereby incorporated by reference.

A. Principles of Operation

The goals of automatic ventilatory positive airway pressure device of the invention ("AutoVPAP") are:
1. To guarantee an adequate alveolar ventilation during sleep.
2. To maximize wake comfort.
3. To maximize depth of sleep.
4. To minimize cost of initiation of therapy and that, directed towards the above goals, a device in accordance with the invention provides:
   1. Servo-control of minute ventilation to equal or exceed a chosen target.
   2. Unloading of much of the spontaneous resistive work if the subject exceeds the chosen target.
   3. A smooth and physiological pressure waveform whose minimum amplitude will unload much but not all of spontaneous elastic work if the subject just exceeds the chosen target.
   4. A mechanism for automatically establishing the target during an awake learning session in subjects who have adequate $PCO_2$ in the daytime and who deteriorate only during sleep.

1. Servo-Ventilation: Choosing a Target

A servo-ventilator can guarantee a minimum ventilation, and thereby prevent the component of REM hypoxia due to hypoventilation. The methodology for choosing the target ventilation may depend upon the patient's condition.

1. Acutely Decompensated Subjects

In subjects who are acutely decompensated, or in whom the daytime $PCO_2$ is unacceptable, it is necessary for the clinician to empirically determine a target ventilation, for example, by starting at 70 ml/Kg/min, and adjusting according to blood gases.

2. Chronically Stable Subjects

In subjects in whom the daytime awake $PCO_2$ is perhaps not perfect but at least adequate, the device provides a simple facility for automatically determining a target ventilation. Briefly, the device measures the subject's spontaneous ventilation during a partially assisted awake acclimatization session, and sets the target ventilation to equal 90% of the median ventilation during the final 40 minutes of the session. The backup respiratory rate (to be used only if the subject fails to be adequately ventilated) is set to the median respiratory rate during the acclimatization session.

The rationale for setting the target ventilation to 90% rather than 100% of the median awake ventilation is that there will be a 10-15% reduction in metabolic activity during sleep. If the ventilation is set to 90% of the daytime awake ventilation, then to a first approximation, the overnight $PCO_2$ will be held at close to the daytime awake $PCO_2$ during the acclimatization session. Conversely, if the target were set to 100% of the spontaneous awake ventilation, then the patient would be driven to central apnea in NREM sleep. This would produce active vocal cord adduction, resulting in unnecessary delivery of maximum pressure.

2. Equation for Mask Pressure

The instantaneous mask pressure is set according to the following equation:

$$P = P_{eep} + R \cdot f + A \cdot \Pi(\phi)$$

where:

$P_{eep}$ is the pressure at end expiration, used to splint the upper airway, unload intrinsic PEEP, and reduce atelectasis. (It corresponds very loosely with EPAP on a bilevel ventilator.)

f is the respiratory airflow.

$\Phi$ is the instantaneous phase in the respiratory cycle.

Figure 2:
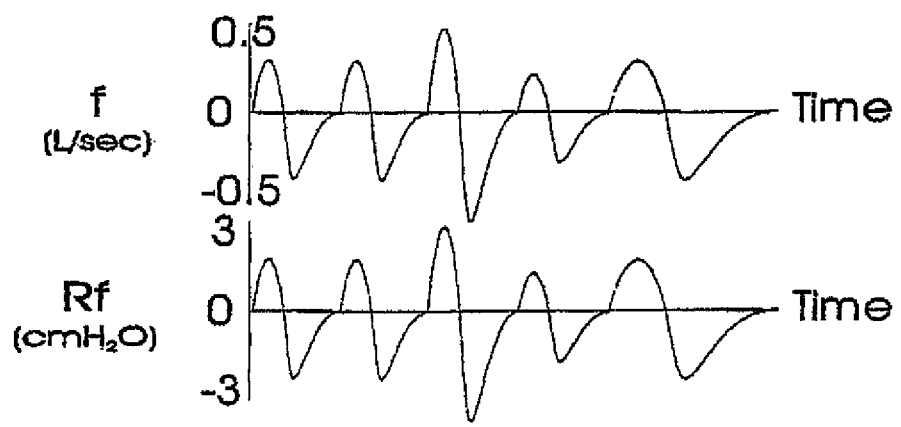
FIG. 2 depicts a typical example of a pressure component of the delivery pressure equation n accordance with the invention.

R is a resistance equal to about 50-80% of the patient's actual airway resistance, and will generally be in the range 2 to 8 $cmH_2O/L/sec$. The $R \cdot f$ term is independent of any estimation of phase, and helps to provide good patient-machine synchronization at the critical moments of start of inspiration and start of expiration. A typical example of the pressure component due to this term for R=6 $cmH_2O/L/sec$ is shown in FIG. 2.

A is the difference between pressure at end inspiration and pressure at end expiration. (It corresponds loosely to the difference between IPAP and EPAP on a bilevel ventilator.)

Figure 3:
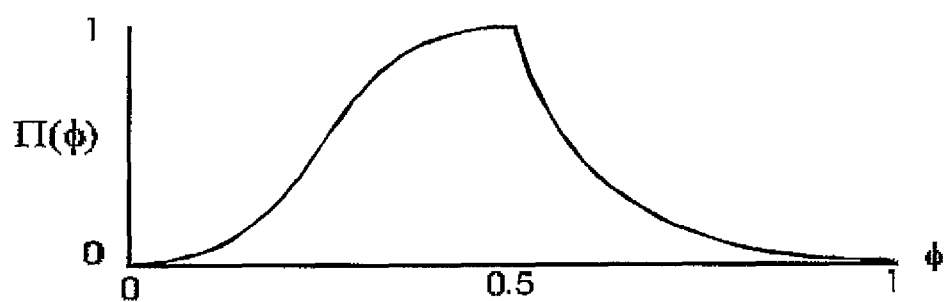
FIG. 3 illustrates a waveform template in accordance with the invention.

$\pi(\Phi)$ is a pressure waveform template which, providing the patient is being ventilated at or above the target ventilation, is shown in FIG. 3. It should be noted that the pressure waveform template is flat (no change with time) at three places: at the start of inspiration ($\Phi$=0), just before end inspiration ($\Phi$=0.5), and at end expiration ($\Phi$=1.0). The effect is to make the estimated phase have very little effect on patient-machine synchronization at these critical points.

The pressure modulation amplitude, or swing, A, is automatically adjusted between a physician-selectable maximum and minimum swing, $A_{max}$ and $A_{min}$ respectively, using the following equation:

$$A = -G \int \frac{|f|}{2} - V_{TGT} dt$$

Where $V_{TGT}$ is the chosen target ventilation, and G is the servo-controller gain, which is set to 0.3 $cmH_2O$ increase in support per second for every L/min error in ventilation. If the patient is breathing at above the chosen target ventilation, then the degree of support will fall to the physician-selected minimum swing $A_{min}$. Conversely, if the subject is breathing at less than the target ventilation, the degree of support will increase quite rapidly until either the target ventilation is reached, or until the degree of support reaches $A_{max}$.

Once the degree of support reaches $A_{MAX}$, the shape of the pressure waveform template becomes progressively more square, and therefore more efficient at generating flow, until either the target ventilation is reached or the waveform is maximally square. Thus, AutoVPAP will try initially to treat the patient with a smooth and comfortable waveform, but if this does not work, it uses a progressively more aggressive waveform, until it succeeds.

Figure 4:
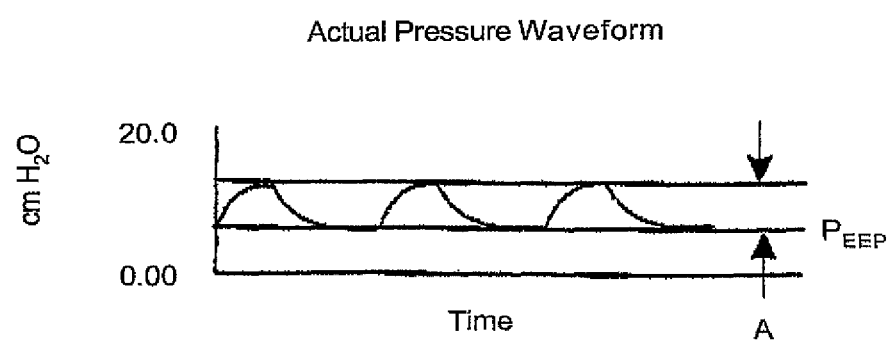
FIG. 4 shows an actual pressure waveform of the delivered pressure from an apparatus of the invention.

The combination of all the terms produces a waveform typically like that shown in FIG. 4.

3. Phase

AutoVPAP uses a 14-rule fuzzy logic algorithm to determine the instantaneous phase $\Phi$ in the machine respiratory cycle. Firstly, there are a series of rules which infer the machine phase from the patient's respiratory airflow, attempting to synchronize directly with the patient. These rules are most strongly active if the patient is breathing at or above the physician-prescribed target ventilation, and the leak is small and steady, but the rules are only weakly active if there is hypopnea or a large or changing leak.

Another rule says that the rate of change of phase equals the patient's recent observed respiratory rate (which is different for inspiration and expiration, to allow for differing times for inspiration and expiration ($T_I$ and $T_E$). This rule allows AutoVPAP to learn the patient's typical respiratory rate and duty cycle. It is also most active if the patient is breathing at or above target, and weak if there is hypopnea or leak.

Finally, there is a rule which says that the phase is increasing at the physician-set backup respiratory rate. This rule is normally almost inactive, but if the ventilation starts to fall below the target, or if there is a long expiratory pause, the rule becomes rapidly more active, hastening the next machine breath.

The net effect of all the rules is that most of the time, when the patient is making reasonable efforts of his own, amplified and augmented by the machine efforts, so that the minute ventilation is at or above target, the machine will synchronize very accurately with the patient.

Conversely, if the patient is making only feeble efforts (roughly speaking, the patient's transdiaphragmatic pressure swing is Jess than about 25% of the machine's pressure swing) the device will no longer be able to always synchronize with the patient.

Even if the patient is centrally apneic, the backup rate will not necessarily be used. The machine may ventilate the patient either faster or slower than the backup rate, depending on lung and chest wall mechanics. There is a tendency for AutoVPAP to use very slow, deep breaths in the face of a high airway resistance, which may be advantageous if it reduces resistive work and avoids air trapping and intrinsic PEEP.

The backup rate will only be used if the patient's ventilation is below the target ventilation, and the machine cannot give any more support by either further increases in swing or by squaring up the waveform template. Since it is a goal of therapy that the patient's ventilation is never below the target, it follows that the backup rate is rarely used. However, if there is an obstructive apnea, or if there is closure of the vocal cords, then the backup rate will be used. This reluctance to use the backup rate makes AutoVPAP very tolerant of errors in setting the backup rate.

4. Comparison with PAV

In operation, the apparatus provides superior results compared to proportional assist ventilation devices. Recall that the equation for mask pressure with AutoVPAP is:

$$P=P_{eep}+R \cdot f + A \cdot \Pi(\phi)$$

whereas the equation for mask pressure for PAV is:

$$P=P_{eep}+R \cdot f + E \cdot \int f dt$$

The term R·f provides resistive unloading in a manner similar to proportional assist ventilation. However, the remainder of the equation is quite different. The most important consequenc'e is that if the patient is centrally apneic, PAV provides no support, whereas AutoVPAP provides increasing support until the target ventilation is achieved. This could potentially be very important for patients with abnormal control of breathing, who could make feeble or no efforts in phasic REM sleep.

B. AutoVPAP Setup Procedure

The steps for setup of the device for an awake learning period to precede regular treatment sessions with the device may be outlined as follows:

1. Switching on

Turn on the blower and computer, connect the two together, and run the control software, as follows. The order is not critical.

Connect the blower to the PC using the serial cable provided. (The cable may be extended using a commercial 9 pin male to female serial cable with all 9 conductors wired straight through.).

Switch on the blower, making sure that the patient is not breathing on the mask, not touching or rattling the hose, and the mask is open to the air (e.g. not blocked by bedclothes etc) or the blower may fail its self test. Wait for the green "READY" light to come on.

Start the computer and run the software.

A few seconds after all steps are completed, flow and pressure data will appear on the long thin graph across the middle of the screen. The time scale is 0-60 seconds. The respiratory airflow graph scale is +−1 L/sec {inspiration upwards), and the mask pressure graph scale is 0-25 cmH$_2$O.

2. Selecting Settings

Settings for the machine can be adjusted using a bank of three double-sliders labeled EEP, SWING, and PEAK respectively. While these sliders are virtual controls that are graphically displayed by the control software, optionally, hardware controls can be included to specify the control settings. The adjustments (1) to (4) below are most easily done in the order shown, because the ranges of some settings are logically determined by others. For example, the sum of the EEP and the swing cannot exceed the maximum peak pressure.

(1) Mode. If the device has multiple modes, the device should be placed in an appropriate mode. The "AutoVPAP" mode can be selected by clicking on an AutoVPAP mode icon that is displayed on a display screen.

(2) Peak and trough pressure. Preferably, the PEAK setting sliders remain at the default values of 22 and 3 cmH$_2$O respectively.

Figure 5:
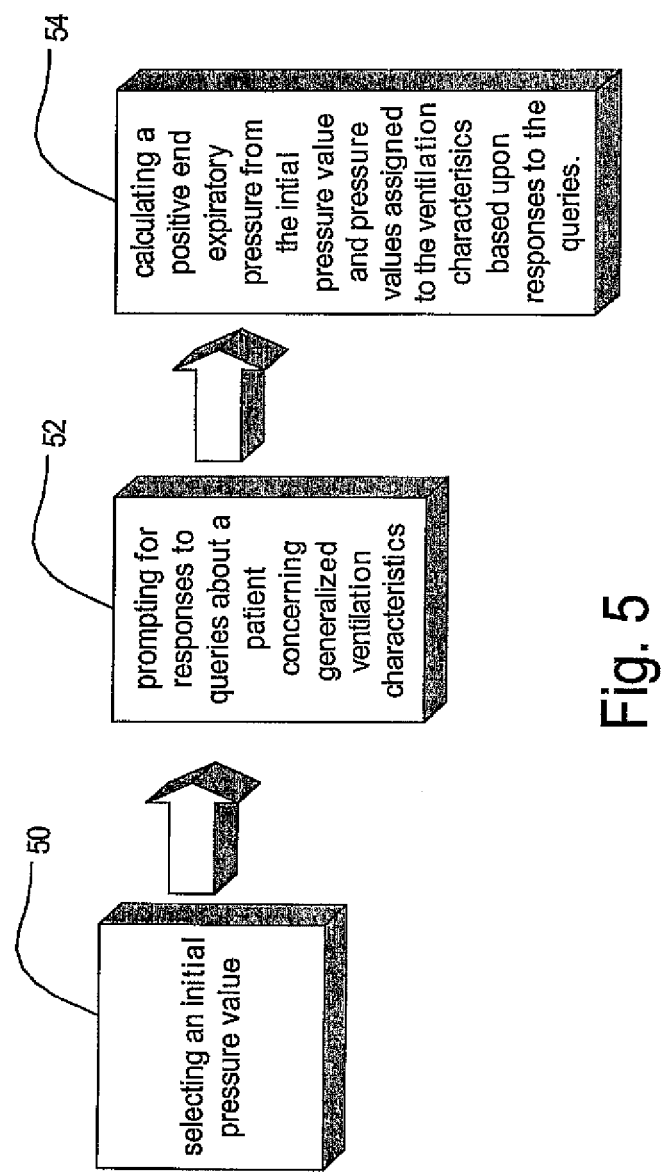
FIG. 5 is a flow chart illustrating steps in a method for determining an end expiration pressure setting for a ventilator of the invention.

(3) End expiratory pressure. The EEP setting, (i.e., the $P_{EEP}$ variable in the pressure delivery formula previously described) may be adjusted according to responses to a series of questions of which the goal is to choose an EEP to minimize upper airway obstruction and unload intrinsic PEEP. The methodology also detailed in the generalized flow chart of FIG. 5 includes a selecting step 50, a prompting step 52 and a calculating step 54. In the selecting step 50, an appropriate starting pressure value is defined. Based upon general ventilation related characteristics that have assigned adjustment pressure values, for example, 2 cmH$_2$O may be assigned to obesity, queries are formed in a prompting step 52. The final setting is calculated in a calculating step 54, the setting is determined as a function of the initial pressure value and one or more of the assigned adjustment pressure values from a set of assigned adjustment pressure values representing the generalized ventilation related characteristics. Preferably, the assigned values are added to the starting pressure value based upon the input responses in the prompting step 52. In this final step, minimum setting limits may be enforced as a result of a particular classification of a patient's condition. The preferred embodiment of the methodology is as follows:

Start at about 4 cmH$_2$O.

If the subject is sleepy (i.e., a state of a lack of wakefulness of the patient), add about 1-2 cmH$_2$1.

If the subject is obese, add about 1-2 cmH$_2$O.

If the subject has a narrow upper airway, add about 1-2 cmH$_2$O.

If the subject has mild, moderate, or severe CAL, the final pressure must be at least in a range of about 5-7 cmH$_2$O or about 5, 6, or 7 cmH$_2$O respectively.

The resultant EEP is in a preferred range of about 4-10 cmH$_2$O.

While this adjustment can be made manually, the device is optionally automated to accomplish the above methodology. To this end, the device is programmed to accomplish the methodology by presenting a series of questions on an output display to the subject/physician and prompt for input on an input device controlled by the microprocessor 16.

Based upon the input responses the EEP may be adjusted automatically by calculating and setting the appropriate EEP.

(4) Pressure Support (swing). Although the preferred device can be set to have a minimum and maximum swing, it is preferred during the learning period to set the maximum and minimum SWING sliders to the same value (i.e., no servo-adjust as yet), chosen to do about half of the patient's awake elastic work. As with the setting determination for the EEP, the methodology for setting the SWING may be performed manually or automated by the ventilator. To this end, the device may be programmed to accomplish the methodology by presenting questions on an output display to the subject/physician and prompt for input on an input device controlled by the microprocessor 16. Based upon the input response the SWING may be adjusted automatically by calculating and setting the appropriate SWING.

Figure 6:
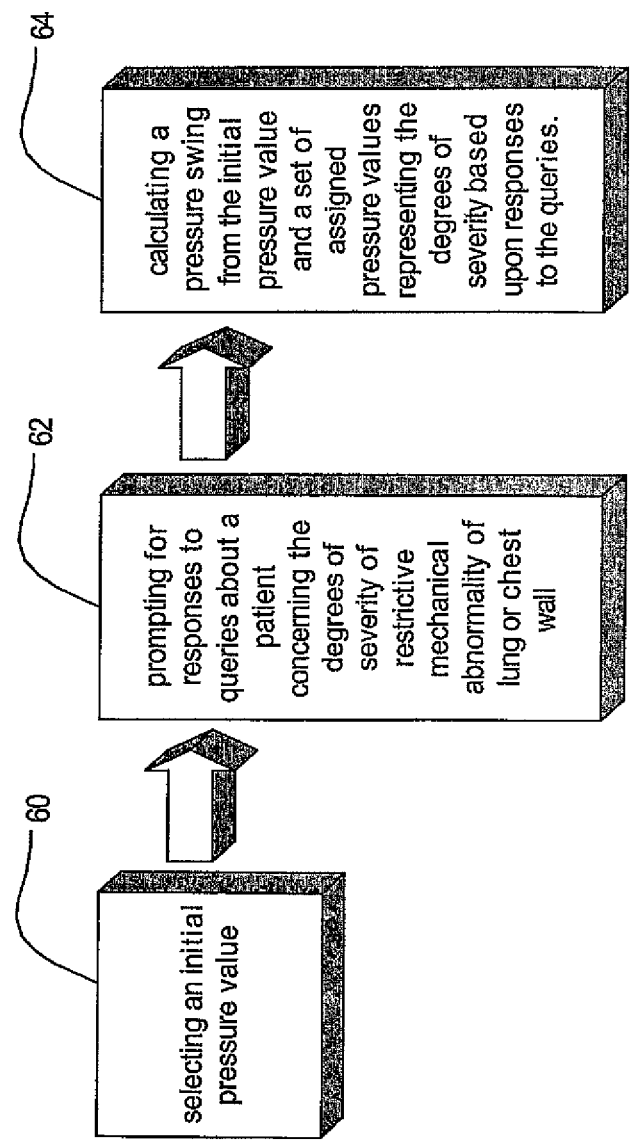
FIG. 6 is a flow chart illustrating steps in a method for determining a resistive unloading pressure setting for a ventilator of the invention.

FIG. 6 outlines the general steps in the methodology. In a selecting step 60, an initial or default swing pressure value is chosen. In a prompting step 62 responses to queries concerning degrees of severity of restrictive mechanical abnormality of lung or chest wall are given. In a calculating step 64, the swing pressure is determined as a function of the initial pressure and a set of assigned adjustment pressures that are assigned to degrees of severity of a restrictive mechanical abnormality in a preferred range of about 2-6 $cmH_2O$. The degrees may have multiple levels and the assigned values increase the initial pressure by a fixed amount for each level of increase in the degree of severity.

In the preferred embodiment, the methodology is as follows:

Start with about 3 $cmH_2O$.

For mild, moderate, or severe restrictive mechanical abnormality of lung or chest wall (excluding neuromuscular or control abnormalities), increase in a range of about 2-6 $cmH_2I$ or by about 2, 4, or 6 $cmH_2O$ respectively.

The resulting swing is in a preferred range of about 3 to 9 $cmH_2O$.

(5) Backup Rate. The backup respiratory rate can be set to 5 breath/min below the patient's expected respiratory rate. This does not need to be at all accurate.

(6) Resistive unloading. Resistive unloading is preferably set to do about 50% to 80% of the patient's expected resistive work. As with prior settings, this preferred methodology for the resistive unloading may be performed manually or automated by the ventilator.

To this end, the device may be programmed to accomplish the methodology by presenting questions on an output display to the subject/physician and prompt for input on an input device controlled by the microprocessor 16. Based upon the input response the resistive unloading may be adjusted automatically by calculating and setting the appropriate value.

Figure 7:
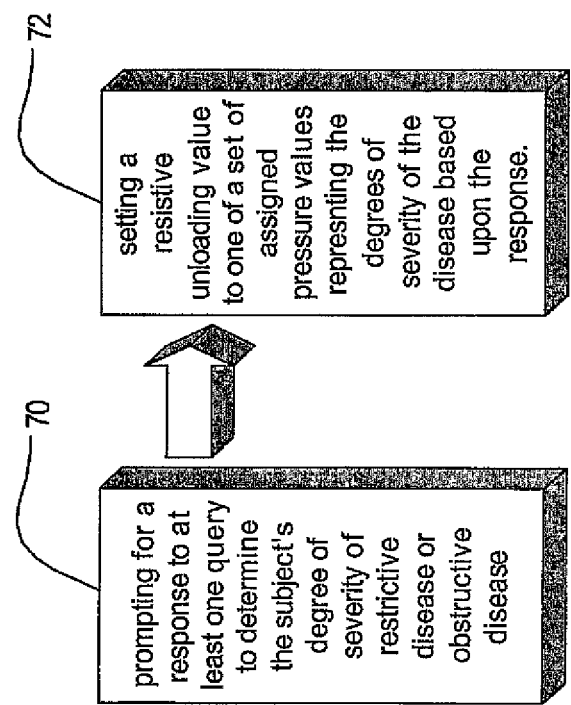
FIG. 7 is a flow chart illustrating steps in a method for determining a resistanceswing pressure setting for a ventilator of the invention.

FIG. 7 outlines general steps in the methodology. In a querying step 70, the physician/user is prompted to determine whether the patient has normal airway resistance or suffers from obstructive or restrictive resistance. The prompting preferably assesses the degree of severity of the identified disease. In a setting the resistance step 72, based upon the responses, assigned resistance values are used to set resistive unloading. The assigned values represent different degrees of severity of the diseases, for example, normal airway resistance (i.e., neuromuscular or control abnormalities), obstructive disease or restrictive disease.

In the preferred embodiment of the invention, the methodology is as follows:

if the patient has normal airway resistance (e.g. neuromuscular or control abnormalities) start with a resistance of about 1 $cmH_2O/L/sec$.

if the patient has mild moderate, or severe obstructive disease, •set to a range of about 4-6 $cmH_2O/L/sec$. or about 4, 6, or 8 $cmH_2O/L/sec$. respectively if the patient has mild, moderate or severe restrictive disease, set to a range of about 3-8 $cmH_2O/L/sec$. or about 3, 4, or 8 $cmH_2O/L/sec$. respectively. This compensates for the narrowed and distorted airways at low volumes.

Thus, the preferred range of resistive unloading is in a range of about 1 to 8 $cmH_2O/L/sec$.

If the above setting of resistive unloading causes the patient to complain that the machine is "pushing them along", or the pressure is oscillating during late expiration, reduce the resistive unloading.

(7) Duty Cycle ($T_1/T_{TOT}$). This setting is not very crucial and a value of 0.4 will suit most patients, because AutoVPAP quickly learns the patient's duty cycle. However, for patients with moderate or severe dynamic airway compression requiring very long expiratory times, a shorter duty cycle, say 0.3 or 0.2 could be used.

(8) Other settings. The other settings should be left at their default values as follows:

| | |
|---|---|
| Wait | Minimum |
| Shape | Maximum |
| Servo Gain | Maximum |

3. Summary of Initial Settings

Remember that the object of all the above settings is to unload as much as possible of the patient's awake ventilatory work without making the patient uncomfortable due to excessive pressures.

The subject may now breathe on the device.

4. Supplemental Oxygen

If necessary, supplemental oxygen is added to the mask, at up to 4 L/min, in order to maintain awake arterial haemoglobin oxygen saturation at or above 90%.

5. Learning Period

Once the subject is comfortable, and the mask has been checked for leaks, it is time to commence the "learning" period, which lasts 1 hour. During this period, the subject is encouraged to watch television or read a book, is asked not to engage in conversation, to concentrate on the television rather than on breathing, and to avoid falling asleep.

To start the learning period, click on the FULL mode icon, which is the right-most of the six mode icons at the top of the screen.

The device records the subject's spontaneous partially assisted ventilation, for example, by determining minute volume, over a 1 hour period, and at the end of the hour automatically sets the target ventilation to equal 90% of the median ventilation during the final 40 minutes. The first 20 minutes are discarded to permit the patient time to settle and to become absorbed by the television program. The median is chosen, rather than the mean, in order to be relatively immune to transients such as coughing or microsleeps. The one hour period serves the dual function of learning the patient's spontaneous awake ventilation, and of acclimatizing the subject to therapy.

The time into the hour is displayed at the bottom right of the screen. At the end of the hour, the device will automatically drop out of the learning mode, and back into the AutoVPAP treatment mode. The patient will not usually notice anything happen at this time. However, the screen will grey out for a period of ten seconds or so, and some of the sliders will move to new positions.

Once the learning period is over, most of the sliders will be in the positions that you set prior to entering the learning period, with the following exceptions:

Target ventilation will have been set to 90% of the median ventilation during the last 40 minutes of the learning period.

Backup rate will have been set to the median respiratory rate during the learning period.

Maximum swing will have been set to 22 minus the EEP, which is as high as it will go.

Additional details concerning a learning period are the subject of U.S. patent application Ser. No. 09/799,260 filed on Mar. 5, 2001, the disclosure of which is hereby incorporated by reference.

6. Additional Adjustments

Figure 8:
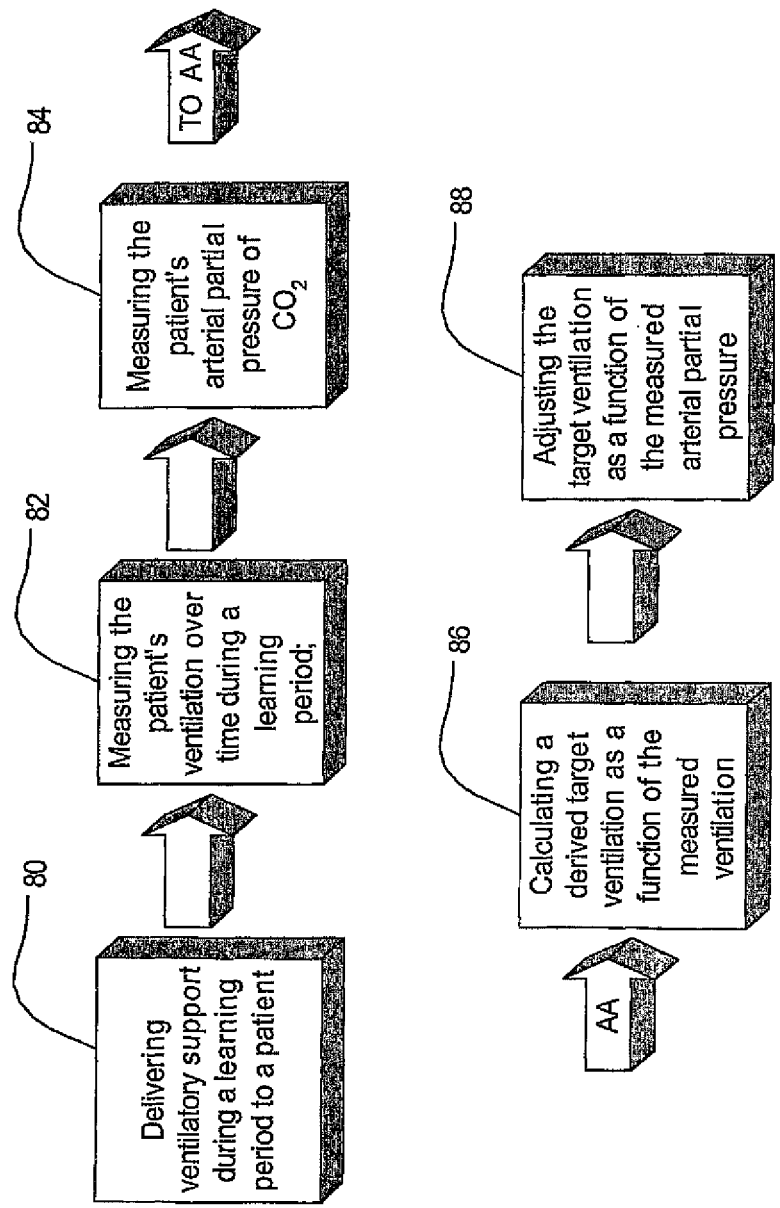
FIG. 8 is a flow chart illustrating steps in a method for determining a target ventilation setting for a ventilator of the invention.

At the end of the learning period, the above settings should be reviewed, to make sure that they are sensible. Optionally, further adjustments to the settings may be made. At present, the only suggested adjustment is to increase the target ventilation slightly in patients who are struggling to maintain an adequate awake $PCO_2$. A flowchart summarizing the steps in the methodology is depicted in FIG. 8. In a delivering step 80, ventilatory support is delivered to the patient during a learning period. In a measuring ventilation step 82 and measuring $PCO_2$ step 84, patient ventilation related characteristics are measured. In a calculating step 86, a target is derived from the measured ventilation. Finally, in an adjusting step 88, the calculated target ventilation is adjusted by formulae which makes use of the measured $PCO_2$. The preferred embodiment of the adjustment methodology is as follows:

For subjects with a daytime arterial $PCO_2$ above about 50 mmHg, increase target by about 1% per mmHg (e.g. 10% at 60 mmHg).

For subjects with a daytime arterial $PCO_2$ below about 50 mmHg, decrease target by about 0.5% per mmHg (e.g. 85% at 40 mmHg).

Of course, these adjustments may be made manually. Alternatively, the machine has programming instructions to automate the methodology after the learning period based upon measured or derived daytime arterial $PCO_2$ values. For example, the device makes the automated measurements with the addition of apparatus to measure daytime arterial $PCO_2$ levels that provides data as input signals to the controller of the device. Alternatively, the device can prompt the user/physician to enter the pertinent measurement data acquired by separate equipment. An automated apparatus for such measurements is disclosed in U.S. Pat. No. 5,630,413. Upon entry or recording of the data, the device calculates the modified ventilation target as a function of the measured daytime arterial $PCO_2$ and a threshold by either of the following formulae depending on the value of the measured $PCO_2$:

$$V_{TGT\text{-}adjusted} = V_{TGT\text{-}learned} * [1 + ((|H - PCO_2|) * 0.001)]$$
(if $PCO_2 > H$)

$$V_{TGT\text{-}adjusted} = V_{TGT\text{-}learned} * [1 - ((|H - PCO_2|) * 0.005)]$$
(if $PCO_2 < H$)

Where:

$PCO_2$ is the measure of daytime arterial partial pressure of CO2

H is a threshold value of preferably about 50 mmHg.

Disconnecting and Switching Off

Once you have checked the final settings, the blower is now ready for long term home therapy.

The blower may be disconnected from the computer, the computer switched off, and the blower switched off. This can be done in any order. The blower will remember the settings. It is not necessary to disconnect if you do not want to.

Optional Awake Confirmation Period

If there is any clinical cause for doubt, the subject could be permitted to continue for an additional hour at this new "treatment mode" setting, and arterialized capillary blood $PCO_2$ or arterial $PCO_2$ taken, to confirm that the subject is not being over-ventilated. While manual measurements may be taken, the device may be optionally equipped to self test the patient's $PCO_2$ level. For example, an automated device for measuring $PCO_2$ as previously disclosed may be configured with the device to make a measurement during a testing mode following the first "treatment mode." The measurement may be compared by the processor with acceptable levels of $PCO_2$ stored in the device. Those skilled in the art will understand the $PCO_2$ levels that would indicate such over ventilation. In response, the device may optionally issue an alarm or prevent further treatment if the comparison of the $PCO_2$ level indicates over-ventilation.

Although the invention has been described with reference to particular embodiments, it is to be understood that these embodiments are merely illustrative of an application of the principles of the invention. Numerous modifications, in addition to the illustrative embodiments of the invention discussed herein may be made and other arrangements may be devised without departing from the spirit and scope of the invention.

The invention claimed is:

1. An automated method for determining a target ventilation setting of a ventilator, the method comprising:

measuring a patient's partial pressure of $CO_2$ and ventilation during a partially-assisted awake acclimatization respiratory session, determining whether the patient's partial pressure of $CO_2$ is adequate; and when the patient's measured partial pressure of $CO_2$ is adequate, automatically calculating a target ventilation based on the measured ventilation, the calculated target ventilation is adjusted based on different functions depending on whether the patient's measured partial pressure of $CO_2$ is determined to be above or below a predetermined threshold, the calculated target ventilation is adjusted by multiplying (a) the calculated target ventilation by (b) a function that includes a product of (1) a difference between a measure of the patient's partial pressure of $CO_2$ and a partial pressure threshold value and (2) a percentage value;

adjusting the ventilator target ventilation setting to the adjusted target ventilation, and delivering servo controlled ventilator support to the patient according to the adjusted target ventilation setting, wherein the percentage value differs depending on whether the patient's partial pressure of $CO_2$ is greater than or less than the predetermined threshold.

2. The method of claim 1, wherein when the patient's measured partial pressure of $CO_2$ is inadequate, setting the target ventilation from empirical data.

3. The method of claim 2, wherein when the patient's measured partial pressure of $CO_2$ is unacceptable, setting the target ventilation at 70 ml/Kg/min.

4. The method of claim 2, wherein the target ventilation is further adjusted according to blood gases.

5. The method of claim 4, wherein the target ventilation is set at 90% of a median ventilation of the session.

6. The method of claim 4, further comprising setting a backup rate to a median respiratory rate during the awake acclimatization respiratory session.

7. The method of claim 4, further comprising manually making additional adjustments to the target ventilation based on the partial pressure of $CO_2$.

8. The method of claim 1, wherein when the patient's measured partial pressure of $CO_2$ is adequate, further measuring the patient's spontaneous ventilation during the partially assisted awake acclimatization respiratory session and setting the target ventilation based on the session.

9. The method of claim 8, wherein the awake acclimatization respiratory session extends for 60 minutes and the target ventilation is set at 90% of a median ventilation of a final 40 minutes of the session.

10. The method of claim 1, wherein the calculated target ventilation is adjusted from an absolute value of the difference.

11. The method of claim 1, wherein the percentage value is 1%.

12. The method of claim 1, wherein the percentage value is 0.5%.

13. The method of claim 1, wherein, when the patient's measured partial pressure of $CO_2$ is equal to a partial pressure threshold value, the target ventilation is calculated without the patient's partial pressure of $CO_2$.

14. The method of claim 1, wherein further comprising receiving input comprising the patient's general ventilation related characteristics and determining, from the general ventilation related characteristics, adjustable settings for unloading the patent's awake ventilatory work.

15. An apparatus for automatically determining a target ventilation setting of a ventilator, the apparatus comprising:
    a servo-controlled blower for providing controlled pressurized air to a patient;
    a transducer operable to generate a flow signal representative of patient airflow;
    a blood gas monitor to generate a $PCO_2$ signal representative of a measure of patient partial pressure of $CO_2$; and
    a processor configured using instructions stored in a memory to
    (a) measure a patient's partial pressure of $CO_2$ and ventilation during a partially-assisted awake acclimatization respiratory session,
    (b) access data from the flow signal and the $PCO_2$ signal, and
    (c) when the patient's measure of partial pressure of $CO_2$ is adequate, automatically calculate a target ventilation based on the ventilation measure form the partially-assisted awake acclimatization respiratory session,
    the target ventilation being calculated based on different functions depending on whether the patient's measure of partial pressure of $CO_2$ is determined to be above or below a predetermined threshold,
    the calculated target ventilation is adjusted by multiplying (a) the calculated target ventilation by (b) a function that includes a product of (1) a difference between a measure of the patient's partial pressure of $CO_2$ and a partial pressure threshold value and (2) a percentage value;
    adjusting the ventilator target ventilation setting to the adjusted target ventilation,
    wherein the percentage value differs depending on whether the patient's partial pressure of $CO_2$ is greater than or less than the predetermined threshold.

16. The apparatus of claim 15, wherein the target ventilation is set at 70 ml/Kg/min when the patient's measure of partial pressure of $CO_2$ is inadequate.

17. The apparatus of claim 15, wherein the processor is further operable to adjust the target ventilation based on measurements by the blood gas monitor.

18. The apparatus of claim 15, wherein the processor is operable to automatically set the target ventilation based on a patient's spontaneous ventilation during the partially-assisted awake acclimatization respiratory session when the processor determines that the patient's partial pressure of $CO_2$ is adequate.

19. The apparatus of claim 18, wherein the target ventilation is set at 90% of a median ventilation of the session.

20. The apparatus of claim 19, wherein the awake acclimatization respiratory session extends for 60 minutes and the target ventilation is set at 90% of a median ventilation of a final 40 minutes of the session.

21. The apparatus of claim 18, wherein the processor is further configured to set a backup rate to a median respiratory rate based on the awake acclimatization respiratory session.

22. The apparatus of claim 18, wherein the processor is configured to receive additional adjustments to the target ventilation from a user.

23. The apparatus of claim 15, wherein the calculated target ventilation is adjusted from an absolute value of the difference.

24. The apparatus of claim 15, wherein the percentage value differs depending on whether the patent's partial pressure of $CO_2$ is greater or less than the partial pressure predetermined threshold value.

25. The apparatus of claim 24, wherein the percentage value is 1%.

26. The apparatus of claim 24, wherein the percentage value is 0.5%.

27. The apparatus of claim 15, wherein, when the patient's measure of partial pressure of $CO_2$ is equal to a partial pressure threshold value, the target ventilation is calculated without the patient's partial pressure of $CO_2$.

28. The apparatus of claim 15, wherein the processor is configured to control the servo-controlled blower in accordance with adjustable settings for unloading awake ventilatory work of the patient calculated from input general ventilation related characteristics of the patient.

* * * * *